United States Patent [19]

Hamann et al.

[11] Patent Number: 5,942,647
[45] Date of Patent: Aug. 24, 1999

[54] PROCESS FOR THE CATALYTIC PREPARATION OF ALKALI METAL ALKOXIDES

[75] Inventors: Carl Heinz Hamann, Ovelgoenne; Peter Schmittinger, Niederkassel, both of Germany

[73] Assignee: Huels Aktiengesellschaft, Marl, Germany

[21] Appl. No.: 08/864,939

[22] Filed: May 29, 1997

[30] Foreign Application Priority Data

May 29, 1996 [DE] Germany .............................. 196 21 466

[51] Int. Cl.$^6$ ...................................................... C07C 31/30
[52] U.S. Cl. ................................................................ 568/851
[58] Field of Search ................................................ 568/851

[56] References Cited

U.S. PATENT DOCUMENTS 4,596,895  6/1986  Auscner et al. .
5,262,133  11/1993  Adams et al. .

*Primary Examiner*—Michael L. Shippen
*Attorney, Agent, or Firm*—Oblon, Spivak, McClelland, Maier & Neustadt, P.C.

[57] ABSTRACT

Catalysts used for the catalytic preparation of alkali metal alkoxides from the alcohol and alkali metal amalgams are selected from the group consisting of carbides and nitrides of metals of group VIa of the Periodic Table, and titanium carbide.

9 Claims, No Drawings

PROCESS FOR THE CATALYTIC PREPARATION OF ALKALI METAL ALKOXIDES

BACKGROUND OF THE INVENTION

1. Field of the Invention

The invention relates to a process for the catalytic preparation of alkali metal alkoxides from alkali metal amalgams and alcohols.

2. Description of the Background

Alkali metal alkoxides, particularly those whose alcohol component contains up to 4 carbon atoms, are valuable chemicals. They are used, for example, as catalysts in the synthesis of many organic compounds. This has given predominantly the alkoxides of sodium and potassium practical importance. A number of methods are known for preparing alkali metal alkoxides [F. A. Dickes, Ber. Dtsch. Chem. Ges. 63, 2753 (1930)]. Thus, solutions of alkali metal hydroxides in an alcohol contain alkali metal alkoxide in equilibrium. Removal of the water present in this equilibrium, for example by distillation, gives pure alkali metal alkoxides. However, particularly in the case of low-boiling alcohols, a great deal of energy is required for this method of shifting the equilibrium.

Pure alkali metal alkoxides are obtained directly by dissolving an alkali metal in the corresponding alcohol. Thus, sodium and potassium react violently with lower aliphatic alcohols such as methanol and ethanol, giving off hydrogen. Higher alcohols such as propanols and butanols are preferably reacted with the alkali metals above the melting point of the latter, if desired under pressure and with stirring. The method of preparing the alkali metal alkoxides directly from metal and alcohol hardly comes into question for a commercial process, because the alkali metals required as starting materials are too expensive.

It is more economical to use, as a source of alkali metal, the liquid alkali metal amalgam formed in chloralkali electrolysis by the mercury method.

The reaction of alkali metal amalgam with alcohols and also the use of catalysts for this reaction are known.

R. B. MacMullin, Chemical Engineering Progress, September 1950, p. 440, mentions, inter alia, the reaction of alkali metal amalgam with methanol in a reactor containing graphite as catalyst. In U.S. Pat. No. 2,336,045 and 2,761,880, materials which are not amalgamated, for example, iron, graphite or mixtures thereof, are proposed as catalysts. U.S. Pat. No. 2,069,403 describes metal meshes comprising heavy metal alloys as catalysts.

The process according to the European Patent 0 177 768 enables the reaction between the amalgam and the alcohol to be accelerated significantly. For the reaction, use is made of a bed of particulate anthracite whose surface is coated with heavy metal oxide or a mixture of heavy metal oxides. Amalgam and alcohol are fed in continuously according to the countercurrent principle; the products are taken off continuously.

In this reaction, the combination of the oxides of nickel and molybdenum has a particularly high activity.

Preference is given to reacting aliphatic alcohols having from 1 to 4 carbon atoms. However, other alcohols can also be used as the starting material in this process, for example, aliphatic alcohols having more than 4 carbon atoms.

However, the prior art thus described is still unsatisfactory. For example, only from 60 to 70% of the sodium introduced in the amalgam are reacted with methanol. A second process step for removing the remaining alkali metal from the amalgam thus remains indispensable. In the case of the reaction of sodium amalgam with ethanol, the proportion which reacts is only from 40 to 50%. Moreover, the life of the oxide-coated catalyst is unsatisfactory. Over the course of about one year, the proportion which reacts drops so much that the catalyst has to be replaced.

It is therefore an object of the present invention to develop a process which avoids the above-mentioned disadvantages.

SUMMARY OF THE INVENTION

Applicants have invented a process for the catalytic preparation of one or more alkali metal alkoxides from the reaction of one or more alkali metal amalgams and one or more alcohols, which comprises carrying out the reaction in the presence of at least one catalyst selected from the group consisting of carbides and nitrides of the metals chromium, molybdenum and tungsten, and titanium carbide.

DETAILED DESCRIPTION OF THE INVENTION

According to the process of the invention, preference is given to reacting aliphatic alcohols having from 1 to 4 carbon atoms. However, other alcohols can also be used as starting material in this process, for example aliphatic alcohols having more than 4 carbon atoms.

The reaction between the amalgam and the alcohol proceeds continuously or batchwise at a high rate, so that high space-time yields are achieved.

It has been found that the decomposition of alkali metal amalgams is accelerated significantly better by carbides and nitrides of metals of group VIa of the Periodic Table, or titanium carbide, than by the heavy metal oxides currently used. When using particulate unsupported material comprising these substances in the model reactor described in Example 1, the following reaction times were observed for the reaction of sodium amalgam with methanol: tungsten carbide 0.6 min, chromium nitride 1 min, titanium carbide 1.7 min, molybdenum carbide 1.8 min, chromium carbide 2.2 min.

For cost reasons, support materials for the catalyst selected are required in industrial use.

If, in the case of carbides, a support material comprising carbon (petroleum coke, graphite, anthracite) is used and a coating is produced by reaction of molybdenum with the carbon, a particularly intimate bond between support and active layer is obtained [A. J. Hegedüs, J. Neugebauer, Z. Anorg. Chem. 305, 218 (1990); S. I. Filippov, V. I. Antonenko, Nauchn. Dokl. Vysshei Shkoly Met. No. 3, 5–9 (1959); V. P. Elyukin, Yu. A. Pavlov. S. B. Sheboidaev, Sb. Mosk. Inst. Stali i Spavov No. 49, 23–45 (1968), Y. Isobe, P. Son, M. Miyake, Journal of less common metals 147, 261–268 (1989). A review may be found in Gmelin supplementary volume Al for molybdenum of 1977, pages 85–87]. Catalyst lives of >3 years with only an insignificant drop in the proportion which reacts are thus made possible.

Having generally described this invention, a further understanding can be obtained by reference to certain specific examples which are provided herein for purposes of illustration only and are not intended to be limiting unless otherwise specified.

Examples 1 to 3 Activity of catalyst samples

To assess the activity of the catalyst samples, 100 g of sodium amalgam containing 0.3% by weight of sodium were placed in a model reactor and 10 g of catalyst granules having the same particle size (5–10 mm) in each case were added. This was covered by 100 ml of alcohol. Both the amalgam and the alcohol were simultaneously stirred with the same stirrer. The measure used for the activity was the increase over time in the conductivity at 60° C of the alcoholic alkoxide solutions formed.

The activity measured in this way has been found in practice to be proportional to the space-time yield of industrial reactors.

In this model reactor, various catalysts gave the following times for complete decomposition of the amalgam.

| Example | Catalyst | Reaction Time in Minutes with | | | |
|---|---|---|---|---|---|
| | | Methanol | Ethanol | 1-Propanol | 1-Butanol |
| 1 | Anthracite pieces activated with a mixture of nickel(II) oxide and molybdenum (VI) oxide (catalyst according to EP 85 11 2789) | 5.5 | 11 | 38 | 77 |
| 2 | Petroleum coke, coated with Mo$_2$C | 2.4 | 3.5 | 18 | 38 |
| 3 | Anthracite pieces, coated with Mo$_2$C | 3.3 | not measured | not measured | not measured |

The best decomposition performance by catalysts applied to supports is given by the catalyst of Example 2. The much cheaper catalyst of Example 3 is only insignificantly poorer and likewise allows virtually 100% decomposition. According to the invention, ethoxide can be prepared at a space-time yield which was previously only obtained in the case of methoxide.

The disclosure of priority German patent application 196 21 466.1, filed May 29, 1996, is hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for the catalytic preparation of one or more alkali metal alkoxides from the reaction of one or more alkali metal amalgams and one or more alcohols, which comprises carrying out the reaction in the presence of at least one catalyst selected from the group consisting of carbides and nitrides of the metals chromium and molybdenum. tungsten nitride, and titanium carbide.

2. The process as claimed in claim 1, wherein the catalyst is a carbide supported on a particulate carbon support material, and wherein said carbide is formed by reduction of a metal compound by the carbon on and close to the surface said support.

3. The process as claimed in claim 1, wherein the metal of catalyst is molybdenum.

4. The process as claimed in claim 2, wherein the metal of the catalyst is molybdenum.

5. The process as claimed in claim 1, wherein the alcohol is one or more alcohols selected from the group consisting of aliphatic alcohols having from 1 to 4 carbon atoms.

6. The process as claimed in claim 2, wherein the particulate carbon support material is petroleum coke.

7. The process as claimed in claim 2, wherein the particulate carbon support material is anthracite.

8. The process as claimed in claim 6, wherein the metal of the catalyst is molybdenum.

9. The process as claimed in claim 7, wherein the metal of the catalyst is molybdenum.

\* \* \* \* \*